United States Patent [19]

Sparta

[11] Patent Number: 4,954,346
[45] Date of Patent: Sep. 4, 1990

[54] ORALLY ADMINISTRABLE NIFEDIPINE SOLUTION IN A SOLID LIGHT RESISTANT DOSAGE FORM

[75] Inventor: Gregory Sparta, Boulder, Colo.; Christopher Pelloni, Louisville, Co.; Deborah Winkel, Westminster, Co., all of Colo.

[73] Assignee: Ciba-Geigy Corporation, Ardsley, N.Y.

[21] Appl. No.: 204,060

[22] Filed: Jun. 8, 1988

[51] Int. Cl.$^5$ .............................................. A61K 9/40
[52] U.S. Cl. .................................... 424/456; 424/455; 514/929; 514/962
[58] Field of Search .............................. 424/456, 452

[56] References Cited

U.S. PATENT DOCUMENTS

| | | |
|---|---|---|
| 1,703,377 | 2/1929 | Anderson. |
| 2,624,163 | 1/1953 | Stirn ........................................ 53/5 |
| 2,663,128 | 12/1953 | Stirn et al. ............................... 53/5 |
| 2,720,463 | 10/1955 | Stirn et al. ............................. 106/135 |
| 2,770,553 | 11/1956 | Waldenb ............................... 104/136 |
| 2,799,591 | 0/1957 | Michel et al. ........................ 106/135 |
| 2,799,592 | 7/1957 | Hansen et al. ....................... 106/135 |
| 2,821,821 | 2/1958 | Yen ......................................... 53/14 |
| 2,899,361 | 8/1959 | McMillon .............................. 167/83 |
| 3,394,983 | 7/1968 | Greif et al. ............................... 4/4 |
| 3,436,453 | 4/1969 | Vincent et al. ......................... 424/6 |
| 3,485,847 | 12/1969 | Bossert et al. ....................... 260/295.5 |
| 3,488,359 | 1/1970 | Bossert et al. ....................... 260/295.5 |
| 3,529,043 | 9/1970 | Taylor et al. .......................... 264/15 |
| 3,644,627 | 2/1972 | Bossert et al. ......................... 424/266 |

(List continued on next page.)

FOREIGN PATENT DOCUMENTS 126379 11/1984 European Pat. Off. .
278168 8/1988 European Pat. Off. .
752362 7/1956 United Kingdom .

OTHER PUBLICATIONS

J. Pharmacol. vol. 39, pp. 1044-1046 (1987).
Hom, Drug Development and Industrial Pharmacy vol. 10(2), pp. 275-287 (1984).
Turk et al., International Journal of Pharmaceuticals vol. 41, pp. 227-230 (1988).
Berson et al., J. Am. Chem. Soc. vol. 77, pp. 447-450 (1955a).
Sugimoto et al., Drug Dev. and Industrial Pharmacy vol. 6, No. 2, pp. 137-160 (1980).
Sugimoto et al., Chem. Pharm. Bull. vol. 29, No. 6, pp. 1714-1723 (1981).
Aquasol A Package insert Chem. Abstr. 104:10590x (1986).
Chem. Abstr. 99:110787p (1983).
Chem. Abstr. 98:204478v (1983).
Chem. Abstr. 96:91573k (1982).
Chem. Abstr. 96:91548f (1982).
Chem. Abstr. 103:147089q (1985).
Chem. Abstr. 103:59153a (1985).
Chem. Abstr. 103:92713f (1985).
Chem. Abstr. 102:12362g (1985).
J. Pharma Science vol. 75, No. 10, pp. 999-1002 (10/86).
J. Pharma Science vol. 75, No. 9, pp. 842-846 (9/86).
Abstract of DE 2,822,882 (1987).
J. Chem. Soc. pp. 1835-1841 (1931).
Procardia Package Insert (PDR).

Primary Examiner—Thurman K. Page
Assistant Examiner—Leon R. Horne
Attorney, Agent, or Firm—Irving M. Fishman

[57] ABSTRACT

A solid dosage form having a fill composition encased in a shell composition; the fill composition comprising
(a) 5-60 mg of nifedipine;
(b) a 5-7 membered cyclic pharmaceutically acceptable ingestible carbonate of the formula

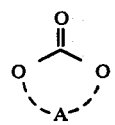

I where A is an alpha,omega-$C_2$-$C_4$ alkylene which is unsubstituted or substituted by at least one $C_1$-$C_4$ alkyl; and
(c) a pharmaceutically acceptable ingestible surfactant having a total of d ring members and being of the formula

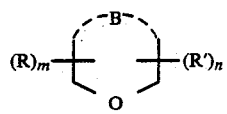

II wherein
B is a $C_{1-4}$-alpha,omega-alkylene;
n is an integer from 0 up to d−1;
m is an integer from 0 up to (d−n−1);
each R is independently H or a $C_{1-4}$alkyl which is unsubstituted or substituted by at least one R';
each R' is independently a hydroxy which is free, etherified by $R^2$, or esterified by $R^3$;
each $R^2$ is a $C_{2-4}$ straight or branched oxyalkylene or a poly ($C_{2-4}$ straight or branched oxyalkylene), the terminal oxygen of which is bound to hydrogen or $R^3$; and each $R^3$ is independently an acyl of a $C_{2-24}$ alkanoic acid or a $C_{4-24}$ alkeneoic acid; provided that there is at least one free hydroxy group, at least one $R^3$ group, and at least 5 now cyclic etherified oxygen atoms per molecule of formula II;
(b) and (c) being present in amounts sufficient to dissolve the nifedipine therein; the shell composition comprising at least gelatin and a dye.

24 Claims, No Drawings

U.S. PATENT DOCUMENTS

| | | | |
|---|---|---|---|
| 3,784,684 | 1/1974 | Bossert et al. | 424/37 |
| 3,819,826 | 6/1974 | D'Alelio | 424/49 |
| 3,912,801 | 10/1975 | Stephens | 423/8 |
| 3,924,004 | 12/1975 | Chang et al. | 424/358 |
| 3,966,903 | 6/1976 | Torii et al. | 424/72 |
| 3,985,705 | 10/1976 | Georgoudis | 260/45.8 A |
| 3,987,004 | 10/1976 | Georgoudis | 260/45.8 A |
| 4,017,615 | 4/1977 | Shastri et al. | 424/241 |
| 4,101,533 | 7/1978 | Lafferty et al. | 528/491 |
| 4,209,298 | 6/1980 | Lazar et al. | 8/582 |
| 4,227,880 | 10/1980 | Hohenegger et al. | 8/524 |
| 4,273,668 | 6/1981 | Crivello | 252/182 |
| 4,279,901 | 7/1981 | Kudla | 424/241 |
| 4,328,245 | 5/1982 | Yu et al. | 424/305 |
| 4,410,545 | 10/1983 | Yu et al. | 424/305 |
| 4,497,823 | 2/1985 | Moore et al. | 514/512 |
| 4,689,233 | 8/1987 | Dvorsky et al. | 424/455 |
| 4,851,228 | 7/1989 | Zentner et al. | 424/456 |

ORALLY ADMINISTRABLE NIFEDIPINE SOLUTION IN A SOLID LIGHT RESISTANT DOSAGE FORM

FIELD OF THE INVENTION

The present invention relates to formulations of the intensely light-sensitive drug nifedipine (4-(2-nitrophenyl)-2,6-dimethyl-3,5-dicarbomethoxy-1,4-dihydropyridine), currently marketed in the U.S. by Pfizer under the name Procardia ® and by Miles under the name Adalat ®. The new formulations are more stable to light than the existing marketed formulations.

Background of the Invention

Nifedipine formulations have been described in U.S. Pat. Nos. 3,485,847; 3,488,359; 3,644,627; 3,784,684; and 4,689,233; as well as in EP No. 0,126,379 and DE No. 2,822,882.

U.S. Pat. No. 3,488,359 mentions formulations generally. Capsules, sugar coated pills and tablets are also mentioned but there is no disclosure of any of the specifics of these dosage forms in this patent. U.S. Pat. Nos. 3,485,847 and 3,644,627 are similar in their disclosure. While an oral form is administered, there is no disclosure of the formulations themselves other than that the active ingredient is combined with a carrier.

U.S. Pat. No. 3,784,684 discloses a capsule composition of nifedipine for oral administration having a fill component and shell component. The fill comprises 1 part nifedipine, 6–50 parts of a $C_{2-3}$ polyalkylene glycol of molecular weight of 200–4000, and 0–10 parts of a $C_{2-8}$ alcohol having 1–3 hydroxy groups. The shell component contains gelatin, a dye, and an opacifier. The recited composition is indicated as preventing nifedipine photolysis during storage and simultaneously permitting rapid and reliable release of nifedipine upon breaking the capsule.

U.S. Pat. No. 4,689,233 deals with increasing the concentration of dissolved nifedipine in capsule fill materials so as to be able to reduce capsule size. The solution found there is to dissolve nifedipine and polyvinylpyrrolidone in a mixture of polyether alcohols of tetrahydrofurfuryl alcohol.

EP No. 126,379 and DE No. 2,822,882 disclose solid compositions where the nifedipine is not in solution at all.

At the present time, the only nifedipine oral composition marketed in which the active agent is in solution is Pfizer's Procardia ® and Miles' Adalat ®, each of which is within the scope of the claims of U.S. Pat. No. 3,784,684. In tests conducted mixing Procardia ® with simulated gastric juice, it has been found that upon exposure there is precipitation of the active agent. Furthermore, the noted precipitation does not always occur to the same degree which theoretically correlates to the human blood level studies indicating that the product has some variability or inconsistency in the rate and extent of absorption of nifedipine in-vivo.

In accelerated light studies, it has further been found that the Procardia ® product had demonstrated significantly more light sensitivity. Observed levels of nitrosophenyl and nitrophenyl derivatives usually exceed USP Pharmacopeial limits.

Cyclic carbonate diesters are mentioned in at least 50 different US patents, most of which relate to their use as reactants for other purposes. However, U.S. Pat. No. 4,273,668; U.S. Pat. No. 4,227,880; U.S. Pat. No. 4,209,298; U.S. Pat. No. 4,101,533; U.S. Pat. No. 3,987,004; U.S. Pat. No. 3,985,705; and U.S. Pat. No. 3,912,801 relate to solubilizing effects of such compounds. Still none of these relate to pharmaceutical uses or to compounds structurally related to nifedipine. On the other hand, U.S. Pat. No. 4,497,823; U.S. Pat. No. 4,410,545; U.S. Pat. No. 4,328,245; U.S. Pat. No. 4,279,901; U.S. Pat. No. 4,017,615; U.S. Pat. No. 3,966,903; U.S. Pat. No. 3,924,004; and U.S. Pat. No. 3,819,826 relate to pharmaceutical products which contain such cyclic diester compounds. However, once again, none of these contains a component which even marginally resembles nifedipine. U.S. Pat. Nos. 4,410,545, and 4,328,245 also mention non-cyclic carbonate diesters which are alternatives for the cyclic carbonate diesters mentioned above. The '545 patent further mentions that the cyclic and non-cyclic diesters are orally administrable.

OBJECTS OF THE INVENTION

It is an object of the invention to provide a nifedipine formulation having improved light stability over that demonstrated by the Procardia ® product.

Another object of the invention is to provide a nifedipine formulation which, upon administration into an acidic environment, such as the stomach, will not precipitate the active agent.

A third object of the invention is to provide a nifedipine formulation which will have greater reproducibility in systemic absorption upon administration thereof to a host's gastro-intestinal tract than that observed both in-vitro and in-vivo with Procardia ®.

SUMMARY OF THE INVENTION

These and other objects have surprisingly been achieved by a formulation of nifedipine comprising a fill composition encased in a shell composition, the shell composition comprising gelatin and a dye and the fill composition comprising (a) from 5–60 mg of nifedipine, (b) a 5–7 membered cyclic pharmaceutically acceptable ingestible carbonate of the formula

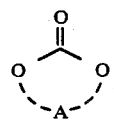

I where A is an alpha,omega-alkylene which is unsubstituted or substituted by at least one $C_1$–$C_4$ alkyl, or a linear pharmaceutically acceptable ingestible carbonate diester of the formula

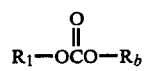

Ia wherein $R_1$ and $R_b$ are each independently $C_1$–$C_{10}$ alkyl; and (c) a pharmaceutically acceptable ingestible surfactant selected from (i) a surfactant having a total of d ring members and being of the formula

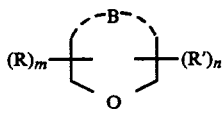

wherein B is a $C_{1-4}$-alpha,omega-alkylene;
n is an integer of from 0 up to and including $d-1$;
m is an integer from 0 up to and including $(d-n-1)$;
each R is independently H or a $C_{1-4}$ alkyl which unsubstituted or substituted by at least one $R^1$;
each $R^1$ is independently a hydroxy which is free, etherified by $R^2$, or esterified by $R^3$;
each $R^2$ is a $C_{2-4}$ straight or branched oxyalkylene or a poly($C_{2-4}$ straight or branched oxyalkylene), the terminal oxygen of which is bound to H or to $R^3$; and
each $R^3$ is independently an acyl of a $C_{2-24}$ alkanoic acid or a $C_{4-24}$ alkenoic acid; provided that the surfactant of formula II has at least one free hydroxy group, and at least one $R^3$ group;
(ii) polyoxyethylene esters of the formula

wherein p is 6–12, on average, and $R_c$ is stearoyl or palmitoyl or a mixture thereof, and $R_d$ is H or the same as $R_c$;
(iii) glycerol polyethylene glycol ricinoleate, glycerol polyethylene glycol oxystearate, and decaglycerin mono-dioleate; and
(iv) polyoxyethylene alkyl ethers of the formula

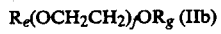

wherein $R_e$ is a $C_{10}$–$C_{18}$ alkyl, f is an integer from about 10 to about 60, and $R_g$ is hydrogen or the same as $R_e$; (b) and (c) being in sufficient amounts so as to dissolve all of the nifedipine therein.

DETAILED DESCRIPTION OF THE INVENTION

The invention is a solid dosage form having a liquid fill formulation encased by a solid shell. The shell formulation must have a wall or film forming member, typically gelatin, having a dye in or on the wall or film. Optional ingredients, which need not be added at all to the shell formulation are a pharmaceutically acceptable plasticizer for the gelatin, an opacifier, and a flavoring agent.

The fill formulation contains 3 required ingredients and may have others. The first required fill component is nifedipine, the active agent. A second required component is a liquid carbonate diester selected from cyclic alkylene carbonates of the formula

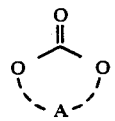

where A is an $C_2$–$C_4$-alpha,omega-alkylene which is unsubstituted or substituted by at least one $C_1$–$C_4$ alkyl and linear carbonate diesters of the formula

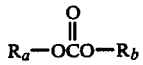

wherein $R_a$ and $R_b$ are each independently $C_{1-10}$ alkyl.

The third required component is a liquid selected from
(i) surfactants of the formula

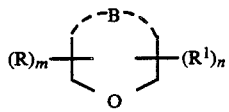

wherein
B is a $C_{1-4}$-alpha,omega-alkylene to form a ring of d atoms; n is an integer from 0 up to and including $d-1$; m is an integer from 0 up to and including $d-n-1$; each R is independently H or a $C_{1-4}$ alkyl which is unsubstituted or substituted by at least one $R^1$;
each $R^1$ is independently a hydroxy group which is free, etherified by $R^2$, or esterified by $R^3$;
each $R^2$ is a $C_{2-4}$ straight or branched oxyalkylene or a poly ($C_{2-4}$ straight or branched oxyalkylene), the terminal oxygen of which is bound to H or R; and
each $R^3$ is independently an acyl of $C_{2-24}$ alkanoic acid or a $C_{4-24}$ alkenoic acid;
provided that each compound of formula II within the present scope has at least one free hydroxy group, at least one $R^3$ group, and preferably has at least 4 non-cyclic etherified oxygen atoms;
(ii) polyoxyethylene esters of the formula

wherein p is 6–8, on average, and $R_c$ is stearoyl or palmitoyl or a mixture thereof, and $R_d$ is hydrogen or the same as $R_c$;
(iii) glycerol polyethylene glycol ricinoleate, glycerol polyethylene glycol oxystearate, and decaglycerol mono-dioleate, and
(iv) polyoxyethylene alkyl ethers of the formula

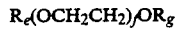

wherein $R_e$ is a $C_{10}$–$C_{18}$ alkyl and f is an integer of from about 10 to about 60, and $R_g$ is hydrogen or the same as $R_e$.

In addition thereto, the fill composition may contain any of a number of pharmaceutical adjuvants such as flavoring agents (such as essential oils, for example peppermint oil, lemon oil, etc.), antioxidants (such as butylated hydroxytoluene up to about 0.5%, butylated hydroxyanisole up to about 0.5%, ascorbic acid, citric acid, sodium metabisulfite, etc.), preservatives (such as sorbic acid, potassium sorbate, methylparaben, ethylparaben, propylparaben, etc.), sweeteners (such as saccharin, sodium saccharin, aspartame, glycrrhizinic acid ammonium salt, hydrogenated glucose syrup, etc.), various dyes and opacifiers, etc.; however, none of these are required for the invention. Still further components which may be present in the fill composition, but are not required, include water, ethanol, glycerin, and propylene glycol.

As stated above, the shell, typically gelatin, has an optional plasticizer present. When the plasticizer is present, soft gelatin capsules are produced; when absent, hard gelatin capsules are produced.

Typical pharmaceutically acceptable plasticizers for gelatin include without limitation include glycerin, sorbitol, propylene glycol, or other polyhydric plasticizers, preferably glycerin.

Usually, when present, the plasticizer is present in the gelatin in an amount of up to 65% by weight of the shell formulation, preferably up to 50%, more preferably 20-40%, still more preferably 30-35% by weight of the shell formulation. Most preferably, the plasticizer is present in an amount of about 35% by weight of the shell formulation.

The dye is preferably selected from those having significant absorption peaks over most of the UV range. Preferably the dye is an FD&C red dye, most preferably FD&C Red Dye 40. Other suitable dyes include FD&C Red 3, FD&C Red 2, FD&C Red 33, FD&C Yellow 6, and FD&C Yellow 5. Still others, which are suitable but not as preferable, include D&C Yellow 10, D&C Red 8, FD&C Red 9, natural colors of caramel, and beta carotene.

The dye is present in the shell formulation in an amount of about 0.75%, preferably 1% by weight up to and beyond the limit of its solubility in the formulation. Exceeding the limit of solubility would produce a speckled capsule, and may be desirable from some aesthetic points of view. Preferably it is present in an amount of about 1.2% to about 3.0%, more preferably about 1.4% to about 2.2% by weight based on the total shell formulation weight.

The most advantageous shell formulation consists of about 160-180 parts of gelatin, 90-100 parts of glycerin and 3-4.5 parts of FD&C Red Dye 40, all parts being by weight.

The other optional shell ingredients, i.e. preservatives, opacifiers, sweeteners, and flavoring agents, can be selected from those known in the art and used in amounts typically known in the art. Preservatives include parabens (methyl, ethyl, and/or propyl) up to about 2%, sorbic acid, and potassium sorbate. Suitable opacifiers are mentioned in U.S. Pat. Nos. 3,784,684 and 4,689,233. Typically included opacifiers are red, brown, black or yellow iron oxides up to about 5 mg of elemental iron per total daily dosage, titanium dioxide at about 0.2 to about 1.2%, aluminum hydrate, aluminum hydroxide, calcium sulfate, magnesium carbonate, calcium carbonate, and others known in the art. Sweeteners include sucrose as well as those mentioned below as optional fill component sweeteners. Flavoring agents include a multitude of essential oils well known to the formulation chemist, peppermint and/or lemon being particularly preferred. They may be used in their art recognized amounts. An additional optional ingredient may also be fumaric acid which helps reduce aldehydic tanning of gelatin. When present, the fumaric acid is in a concentration of up to about 1% of the gelatin present.

The fill composition, as previously mentioned has 3 required components, a carbonate diester, a surfactant, and nifedipine. The active agent nifedipine is present in an amount of 5-60 mg, preferably 5-30 mg, more preferably about 10- about 20 mg per dosage unit.

The carbonate diester is selected from the cyclic 1,3-dioxa-2-ones of formula I and the linear carbonate diesters of formula Ia. As between the carbonates of formula I and formula Ia, those of formula I are preferred.

The 1,3-dioxa-2-one compound of the formula I preferably has a total of 4-6 ring members, most preferably 5 ring members so that A is preferably a saturated alpha,omega-alkylene of one to 3 carbon atoms, most preferably of 2 carbon atoms. A may be unsubstituted, but preferably one or more of the carbon atoms thereof has a $C_{1-4}$ alkyl substituent, most preferably A is monosubstituted by a $C_{1-4}$ alkyl group. The $C_{1-4}$ substituent on A is preferably methyl, ethyl, propyl or isopropyl, more preferably methyl or ethyl, most preferably methyl. The most preferred compound of formula I in the instant invention is propylene carbonate, having the formula

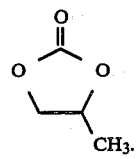

III

The linear carbonate diester of formula Ia is preferably a carbonate di(lower alkyl) ester, that is $R_a$ and $R_b$ are preferably independently $C_{1-7}$ alkyl, more preferably $C_{1-4}$ alkyl. Still more preferably, they are selected from methyl, ethyl, and isopropyl; most preferably each is ethyl. While $R_a$ and $R_b$ need not be the same, it is preferably that they are.

The surfactant must be pharmaceutically acceptable and ingestible. It is selected from those of formulae II, IIa, IIb, glycerol polyethylene glycol ricinoleate, glycerol polyethylene glycol oxystearate and decaglycerol mono-dioleate. Of these, those of formula II are preferred.

The cyclic ether of formula II has a total of 4-7 ring members, i.e. B is a $C_{1-4}$-alpha,omega-alkylene, but preferably has 4-6 ring members, most preferably 5 ring members, making B preferably a $C_{1-3}$-alpha,omega-alkylene, most preferably 1,2-ethylene. The substituent R is selected from a hydrogen, and a $C_{1-4}$ alkyl which is unsubstituted or substituted by a group $R^1$, where $R^1$ is a hydroxy, an $R^2$ etherified hydroxy, or an $R^3$ esterified hydroxy. The $R^2$ etherifying group is an oxyalkylene or polyoxyalkylene in which the alkylene group has 2-4 carbons and is straight chain or branched. The $R^3$ esterifying group is an acyl of an alkanoic acid of 2-24 carbons or of an alkenoic acid of 4-24 carbons. Preferably the $R^3$ acyl has an even number of carbon atoms, more preferably 10-20 carbons, still more preferably 12-18 carbons. The total number of non-cyclic ether oxygen atoms in the compound of formula II is preferably at least 4, and preferably less than 40, more preferably from 5-35, even more 10 to 30, still more preferably from 15 to 25, yet more preferably 18-22, most preferably 20. These can be contained in a single polyoxyalkylene chain but need not be. Preferably there is more than one polyoxyalkylene chain present per molecule of formula II, i.e. there is at least two $R^1$ hydroxy groups which are etherified.

Compounds of formula II are available under the tradenames Tweens, Soralte, Monitan, Crillet, Arlacel, Armotan, Span, Sorbester, and others.

Most preferably, the compounds of formula II are selected from compounds of the formula

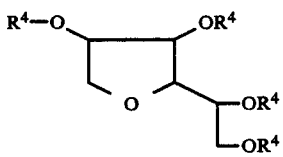

(IV)

where each $R^4$ is independently H, $R^2$ or $R^3$ provided that there is at lest one free hydroxy (whether $R^4$ is H directly or $R^2$ which has a free terminal hydroxy), at least one $R^3$ esterified hydroxy (whether $R^4$ is $R^3$ directly or $R^2$ which is esterified by $R^3$), and at least the number of non-cyclic ether oxygens set out above present. Still more preferably, the compounds of formula II are selected from compounds of the formula

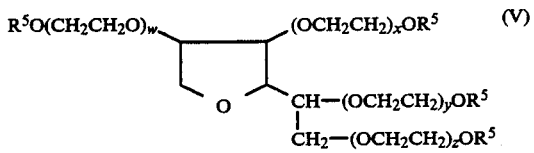

(V)

wherein each of w, x, y, and z is independently 0 to 40, preferably 0 to 20, and the sum of w, x, y, and z being 4–160, preferably 5–80, more preferably 5–40, still more preferably 10–30, even more preferably 15–25, yet more preferably 18–22, most preferably 20; and each $R^5$ independently being H or $R^3$, provided at least one $R^5$ is $R^3$.

The most preferable compounds of formula II and V are available as the polysorbate series of surfactants available under the Tween ® name. Of these, the most preferably is polysorbate 20 having the formula

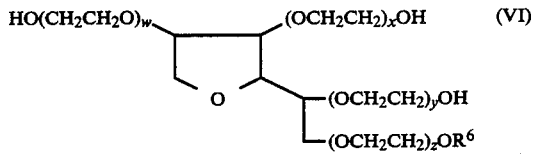

(VI)

The surfactant of formula IIb are preferably those wherein $R_g$ is hydrogen. Another preferred group is that wherein f is 15–30, preferably 20–24. Another preferred group is that wherein $R_e$ is $C_{12}$–$C_{18}$ alkyl. A most preferred subgroup is that wherein f is 20–24, $R_g$ is hydrogen, and $R_e$ is $C_{12-18}$ alkyl. These compounds are typically available under the Cremophor A tradename.

Sources of almost all of the surfactants above can be found in the Handbook of Pharmaceutical Excipients published by the American Pharmaceutical Association.

The surfactant can be used as individual items or as mixtures thereof.

The carbonate diester and the surfactant are present, in part, to dissolve the active agent nifedipine. They are employed in at least the minimum amounts necessary to dissolve the amount of nifedipine in the dosage form and limited as to their maximal content by the largest orally administrable capsule that the animal, preferably a human being, being treated will tolerate. Preferably, the total fill composition will fit within a hard gelatin capsule of up to and including size 000, preferably up to and including size 00, still more preferably up to and including size 0, most preferably up to and including size 1. Preferably, the total fill composition will fit within a 20 minim oblong soft gelatin capsule having a fill volume of 0.986 ml to 1.232 ml, more preferably within a 16 minim oval soft gelatin capsule having a fill volume of a 764 ml to 0.986 ml, most preferably within a 9 minim round soft gelatin capsule having a fill volume of 0.431 ml to 0.554 ml. A highly preferred amount of the mixture of compound of formula I and compound of formula II is about 45 parts to about 720 parts, preferably about 90 parts to about 450 parts, more preferably about 180 parts to about 360 parts by weight for every 10 parts by weight of nifedipine.

The ratio of compound of formula II to compound of formula III, on a weight basis is from 99:1 to 1:99, preferably from 10:1 to 1:10, more preferably from 3:1 to 1:3, still more preferably from 2.5:1 to 1:2.5, yet more preferably 2.0:1 to 1:2.0, even still more preferably about 1.5:1 to about 1:1.5, yet even more preferably about 1.2:1 to about 1:1, most preferably about 1.1:1 to about 1.05:1.

In another embodiment, the compounds of formula I and II are also independently preferably present in an amount of about 40 to 540 parts, more preferably 90–360 parts, and most preferably 160 parts to 195 parts by weight per 10 parts of nifedipine.

The optional fill composition ingredients, such as the flavorings, preservatives, antioxidants, colorants, sweeteners, etc., may each be used in amounts known in the art.

A most preferred fill composition comprises propylene carbonate about 186 parts, polysorbate 20 about 172 parts, nifedipine about 10 parts, and optionally peppermint oil about 1 part, all parts being by weight.

The fill formulations of the instant invention are most advantageously compounded by simply mixing the carbonate with the surfactant and, if necessary, heating to form a homogeneous solution. If heating is used, a temperature below about 140° F., but preferably approximately 120° F., is recommended, but a maximum is limited only by the stability of the fill component materials being heated. Once the homogeneous solution is obtained, the nifedipine is added with stirring until the nifedipine is dissolved. If heating was used to obtain the homogeneous solution, the temperature is preferably maintained at that level, but preferably not in excess of 120° F., until the nifedipine is dissolved. The solution is then cooled, if heating was employed, and ready to be encapsulated or have the optional fill ingredients added and then be encapsulated. Alternatively the optional fill ingredients can be added to either the carbonate or the surfactant or mixture thereof before adding the nifedipine. Also the nifedipine may be added to either the carbonate before adding the surfactant or to the surfactant before adding the carbonate.

The shell formulation is prepared by mixing and melting together the gelatin with water. If soft gelatin capsules are desired, the plasticizer is added in the above step. If hard gelatin capsules are desired, the plasticizer is omitted. After the melt is formed, the dye and any optional ingredients are added thereto to form a gel mass. The mass is then used to encapsulate measured amounts of fill composition in conventional gelatin encapsulation of liquid techniques. In some manufacturing processes of the above formulations, it may be found that minor amounts of gelatin, water, and/or plasticizer find there way into the fill composition. If so, the water is preferably limited to no more than 5% of the fill and the gelatin and plasticizer each preferably to no more than 10% of the fill. However, most preferably, these shell components are not present in the fill at all.

If coloring matter is used as an optional ingredient in the fill composition, the dye in the shell may be reduced or even eliminated.

Each of the components of the shell formulation and the fill formulation are independently known in the art or can be prepared from known starting materials in manners analogous to those material, which are already known.

Synthetic routes to various cyclic carbonate diesters are set forth in U.S. Pat. Nos. 4,483,994; 4,353,831; 4,344,881; 4,332,729; 4,331,604; 4,325,874; 4,247,465; 4,233,221; 3,231,937; 4,226,778; 4,224,223; 4,009,183; 3,923,842; 3,748,345; 3,663,569; 3,535,342; and 3,535,341.

The foregoing invention will be more clearly understood from the following examples which exemplify but do not limit the invention. In all examples, the nifedipine is at all times protected from light unless specifically stated otherwise.

EXAMPLE 1

One thousand nifedipine 10 mg soft gelatin capsules are prepared by mixing 186.05 grams of propylene carbonate with 171.95 grams of polysorbate 20 and the mixture is heated to approximately 120° F. to form a homogeneous solution. 10 Grams of nifedipine is added to the homogeneous solution with stirring; the temperature and stirring are maintained until all of the nifedipine is dissolved. The solution is cooled to room temperature and then encapsulated.

The encapsulating formulation is prepared by mixing and melting together 169.6193 grams of gelatin, 94.6099 g of glycerin, and 19 grams of water. To this melt is added 3.7693 g of FD&C Red Dye No. 40 to form a gel mass. The mass is formed into ribbons and cast into capsules around a measured dose of the fill solution on conventional soft gelatin capsule encapsulation equipment. The filled soft gels resulting therefrom are then dried to remove the desired amount of water.

EXAMPLE 2

The procedure of Example 1 is followed except that after the fill solution is cooled, 1 gram of peppermint oil is added thereto prior to encapsulation.

EXAMPLES 3–20

The procedures of Example 1 are followed except that the stated compounds and amounts in the Table below are used in place of those in Example 1.

| | Compound Replaced | | | |
|---|---|---|---|---|
| Example No. | Plasticizer | Dye | Carbonate | Surfactant |
| 3 | | | | Polysorbate 20: 370 g |
| 4 | | | | Polysorbate 20: 93 g |
| 5 | | | | Polysorbate 40: 172 g |
| 6 | | | | Polysorbate 60: 172 g |
| 7 | | | | Polysorbate 65: 172 g |
| 8 | | | | Polysorbate 80: 172 g |
| 9 | | | | Polysorbate 85: 172 g |
| 10 | | | 1,3-dioxacyclopentan-2-one 186 g | |
| 11 | | | 4-ethyl-1,3-dioxacyclopentan-2-one 186 g | |
| 12 | | | 1,3-dioxacyclohexan-2-one 186 g | |
| 13 | | FD&C Red No. 40 3 g | | |
| 14 | | FD&C Red No. 3 3.8 g | | |
| 15 | | FD&C Yellow No. 6 3.8 g | | |
| 16 | | FD&C Yellow No. 5 3.8 g | | |
| 17 | glycerin 116 g | | | |
| 18 | glycerin 58 g | | | |
| 19 | 0 g | | | |
| 20 | propylene glycol 95 g | | | |

EXAMPLE 21

Nifedipine capsules according to the instant invention (Sample A) were prepared having the following formulation following the procedure of Example 1:

| Shell: | |
|---|---|
| gelatin | 169.6193 parts |
| glycerin | 94.6099 parts |
| water (purified) | 19.000 parts |
| FD&C Red 40 | 3.7693 parts |
| Fill: | |
| Propylene Carbonate | 186.05 parts |
| Polysorbate 20 | 171.95 parts |
| Nifedipine | 10.00 parts |
| Peppermint Oil | 1.00 parts |

For comparison purposes commercially available nifedipine capsules, Procardia ® (Pfizer) were used. (Sample B)

Batches of Samples A and B of Example 22 were prepared and obtained, respectively, and used in human bioequivalence studies wherein volunteers were given 2×10 mg capsules of either Sample A or Sample B on each of days 1 and 7. The design study was a randomized two way crossover one. The dose was administered and blood collected at ½, ¾, 1, 1¼, 1½, 2.0, 2.5, 3, 4, 5, 6, 7, 8, 12, 16 and 24 hours after dosing. Plasma nifedipine levels were determined. The results are summarized below.

|  | Sample A | | | Sample B | | |
| --- | --- | --- | --- | --- | --- | --- |
| Time | Average | STD DEV | (100)STD DEV / AVG | Average | STD DEV | (100)STD DEV / AVG |
| 0.00 | 0.00 | 0.00 | — | 0.00 | 0.00 | — |
| 0.50 | 187.12 | 114.81 | 61.4 | 143.06 | 120.29 | 84.1 |
| 0.75 | 146.28 | 63.25 | 43.2 | 124.21 | 89.37 | 71.9 |
| 1.00 | 113.07 | 36.16 | 32.0 | 93.95 | 63.27 | 67.3 |
| 1.25 | 94.00 | 30.13 | 32.1 | 78.39 | 51.14 | 65.2 |
| 1.50 | 78.51 | 32.37 | 41.2 | 66.02 | 40.45 | 61.3 |
| 2.00 | 54.80 | 24.36 | 44.5 | 49.56 | 31.33 | 63.2 |
| 2.50 | 39.18 | 17.22 | 44.0 | 39.99 | 25.48 | 63.7 |
| 3.00 | 29.75 | 13.54 | 45.7 | 32.79 | 23.34 | 71.2 |
| 4.00 | 18.85 | 8.52 | 45.2 | 23.22 | 12.98 | 55.9 |
| 5.00 | 11.83 | 6.11 | 51.7 | 17.17 | 10.99 | 64.0 |
| 6.00 | 4.76 | 4.94 | 50.6 | 13.29 | 8.87 | 66.7 |
| 8.00 | 5.85 | 3.21 | 54.9 | 7.86 | 5.96 | 75.8 |
| 12.00 | 2.27 | 2.33 | 103 | 3.57 | 4.38 | 123.0 |
| 16.00 | 0.53 | 1.09 | 206 | 1.17 | 2.82 | 241.0 |
| 24.00 | 0.00 | 0.00 | — | 0.28 | 1.15 | 411 |

Comparison of the $$\frac{(100)STD\ DEV}{AVG}$$

(the coefficient of varience) for Samples A and B shows that Sample B exhibits variability in blood levels by the following amounts:

| Time (hrs.) | Excess Variability of Sample B over Sample A |
| --- | --- |
| 0 | 0 |
| 0.5 | 38% |
| 0.75 | 65% |
| 1.00 | 78% |
| 1.25 | 93% |
| 1.50 | 49% |
| 2.00 | 42% |
| 2.50 | 46% |
| 3.00 | 56% |
| 4.00 | 56% |
| 5.00 | 25% |
| 6.00 | 31% |
| 8.00 | 38% |
| 12.00 | 19.4% |
| 16.00 | 17% |
| 24.00 | not applicable |

We claim:

1. A gelatin encapsulated liquid fill formulation of nifedipine which is substantially stable against light degradation condition comprising a capsule wall formulation encasing a capsule fill formulation, said capsule wall formulation comprising gelatin in an amount sufficient to encapsulate said capsule fill composition, with or without a pharmaceutically acceptable, ingestible, plasticizer for gelatin; said fill formulation comprising 5–60 mg of nifedipine, and a mixture of a carbonate and a surfactant in an amount sufficient to dissolve said nifedipine, and in a ratio of carbonate to surfactant of from 99:1 to 1:99, said carbonate being selected from a di-$C_{1-10}$ alkyl carbonate and a compound of the formula

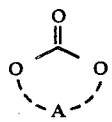   I wherein A is a $C_{1-4}$-alpha,omega-alkylene which is unsubstituted or substituted by $C_{1-4}$ alkyl; said surfactant being selected from compounds of formula II, IIa, and IIb, decaglycerol mono-dioleate, glycerol polyethylene glycol ricinoleate, and glycerol polyethylene glycol oxystearate; said formula II being a substituted cyclic ether having d ring members and being

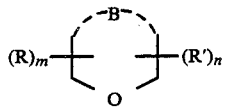   II wherein B is a $C_{1-4}$-alpha,omega-alkylene; n is an integer 0 to $d-1$; m is an integer of from 0 to $(d-n-1)$; each R is each R is independently H or a $C_{1-4}$ alkyl which is unsubstituted or substituted by at least one $R^1$; each $R^1$ is independently a hydroxy which is free, etherified by $R^2$, or esterified by $R^3$, each $R^2$ is a $C_{2-4}$ straight or branched oxyalkylene or poly($C_{2-4}$ straight or branched oxyalkylene), the terminal oxygen of which is bound to H or $R^3$; and each $R^3$ is independently an acyl of a $C_{2-24}$ alkanoic acid or a $C_{4-24}$ alkenoic acid; provided that in each compound of formula II there is at least one free hydroxy group, and at least one $R^3$ group; said formula IIa being

   (IIa)

wherein p is, on average, 6–8, $R_c$ is stearoyl or palmitoyl or mixtures thereof, and $R_d$ is hydrogen or the same as $R_c$; said formula IIb being

   (IIb)

wherein $R_e$ is $C_{10-18}$ alkyl, f is an integer of from about 10 to about 60, and $R_g$ is hydrogen or the same as $R_e$; said gelatin encapsulated liquid fill formulation further comprising a dye in at least one of said shell formulation and said capsule fill formulation.

2. The composition of claim 1 wherein said gelatin plasticizer is present.

3. The composition of claim 1 wherein said gelatin plasticizer is glycerin.

4. The composition of claim 1 wherein said plasticizer is present up to and including 65% by weight of said shell composition.

5. The composition of, claim 1 wherein said dye is present in at least said wall formulation.

6. The composition of claim 1 wherein said dye is an FD&C Red Dye.

7. The composition of claim 1 wherein said dye is FD&C Red Dye No. 40.

8. The composition of claim 1 wherein said dye is present in said wall formulation in an amount of from about 0.75% by weight up to and including its limit of solubility and beyond in said shell formulation.

9. The composition of claim 1 wherein said wall formulation comprises:
gelatin—about 160-180 parts by weight,
glycerin—about 90-100 parts by weight, and
FD&C Red 40—about 3-4.5 parts by weight.

10. The composition of claim 1 wherein said nifedipine is present in about 10- about 20 mg per dosage unit.

11. The composition of claim 1 wherein said carbonate is propylene carbonate of the formula

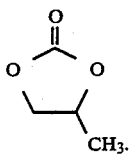
III

12. The composition of claim 1 wherein said surfactant is of the formula

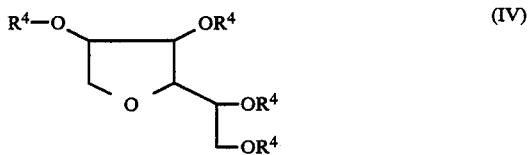
(IV)

wherein $R^4$ is independently H, $R^2$ or $R^3$ with $R^2$ and $R^3$ being as defined in claim 1; provided that each compound of formula IV has at least one free hydroxy, at least one $R^3$ esterified hydroxy, and at least 4 non-cyclic ether oxygen atoms.

13. The composition of claim 1 wherein said compound of formula II is of the formula

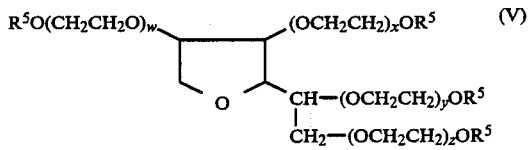
(V)

wherein each of w, x, y and z is independently 0-40 and the sum of w, x, y and z is 5-160; and each $R^5$ is independently H or $R^3$, provided that at least one $R^5$ is H and at least one $R^5$ is $R^3$.

14. The composition of claim 1 wherein said compound of formula II is a polysorbate.

15. The composition of claim 1 wherein the compound of claim 1 is polysorbate 20.

16. The composition of claim 1 wherein said fill formulation comprises:
about 10 parts to about 20 parts by weight of nifedipine and
about 45 parts to about 720 parts by weight combined of a compound of formula I and a compound of formula II.

17. The composition of claim 1 wherein said fill formulation comprises:
nifedipine—about 10- about 20 parts by weight,
propylene carbonate—about 160- about 195 parts by weight, and
polysorbate 20—about 160- about 195 parts by weight.

18. The composition of claim 1 wherein said shell formulation further comprises at least one pharmaceutically acceptable ingestible adjuvant selected from opacifiers, flavorings, sweeteners, antioxidants, preservatives, and fumaric acid.

19. The composition of claim 17 wherein said wall opacifiers are selected from titanium dioxide, iron oxides, aluminum hydrate, talc, aluminum silicate, magnesium oxide, aluminum hydroxide, calcium sulfate, magnesium carbonate, and calcium carbonate; said wall flavorings are selected from essential oils; and said wall preservatives are selected from paraben preservatives, sorbic acid and potassium sorbate; said shell sweeteners are selected from sucrose, saccharin, sodium saccharin, aspartame, glycyrrhizinic acid ammonium salt, and hydrogenated glucose syrup.

20. The composition of claim 1 wherein said fill formulation comprises at least one pharmaceutically acceptable, ingestible adjuvant selected from flavorings, sweeteners, antioxidants, preservatives and opacifiers.

21. The composition of claim 19 wherein said fill flavorings are selected from essential oils; said fill sweeteners are selected from saccharine, sodium saccharin, aspartame, glycyrrhizinic acid ammonium salt, and hydrogenated glucose syrup; said fill antioxidants are selected from butylated hydroxytoluene, butylated hydroxyanisole, ascorbic acid, citric acid, and sodium metabisulfite; said fill preservatives are selected from paraben preservatives, sorbic acid and potassium sorbate; and said opacifiers are selected from iron oxides, titanium dioxide, aluminum hydrate, talc, aluminum silicate, magnesium oxide, aluminum hydroxide, calcium sulfate, magnesium carbonate, and calcium carbonate.

22. The composition of claim 1 wherein said wall formulation comprises:
gelatin—about 160- about 360 mg
glycerin—about 90- about 200 mg
FD&C No. 40—about 3- about 9 mg
and said fill composition comprises:
nifedipine—about 10- about 20 mg
propylene carbonate—about 160- about 390 mg
polysorbate 20—about 160- about 390 mg and
peppermint oil—about 1- about 2 mg
all weights being per dosage unit.

23. The composition of claim 1 which comprises
(a) as a wall formulation:
gelatin—about 170 mg
glycerin—about 95 mg and
FD&C Red 40—about 3.8 mg and
(b) as a fill formulation;
nifedipine—about 10 mg
propylene carbonate—about 186 mg
polysorbate 20—about 172 mg and
peppermint oil about 1 mg.

24. A method of treating a nifedipine responsive condition in a mammal in need thereof comprising administering to said mammal a therapeutically effective amount of a composition of claim 1.

* * * * *